(12) United States Patent
Srocka et al.

(10) Patent No.: US 8,817,089 B2
(45) Date of Patent: Aug. 26, 2014

(54) INSPECTION SYSTEM

(75) Inventors: Bernd Srocka, Berlin (DE); Marko Döring, Dresden (DE)

(73) Assignee: HSEB Dresden GmbH, Dresden (DE)

( * ) Notice: Subject to any disclaimer, the term of this patent is extended or adjusted under 35 U.S.C. 154(b) by 339 days.

(21) Appl. No.: 13/384,267

(22) PCT Filed: Apr. 28, 2010

(86) PCT No.: PCT/EP2010/055741
§ 371 (c)(1),
(2), (4) Date: Jan. 16, 2012

(87) PCT Pub. No.: WO2011/006687
PCT Pub. Date: Jan. 20, 2011

(65) Prior Publication Data
US 2012/0113243 A1    May 10, 2012

(30) Foreign Application Priority Data

Jul. 16, 2009 (DE) .......................... 10 2009 026 187

(51) Int. Cl.
*H04N 7/18* (2006.01)
(52) U.S. Cl.
USPC ............................................................ 348/79
(58) Field of Classification Search
CPC .......... G01N 21/9501; G01N 21/9503; G01N 21/9506
USPC .............. 348/79, 87; 356/237.1, 237.5, 237.2
See application file for complete search history.

(56) References Cited

U.S. PATENT DOCUMENTS

| | | | |
|---|---|---|---|
| 6,553,850 B2 | 4/2003 | Birkner et al. | |
| 7,268,867 B2 | 9/2007 | Vollrath et al. | |
| 2002/0187035 A1 | 12/2002 | Schaefer et al. | |
| 2003/0117596 A1* | 6/2003 | Nishi | 355/51 |
| 2006/0119366 A1 | 6/2006 | Iffland et al. | |
| 2008/0284455 A1* | 11/2008 | Obikane et al. | 324/754 |
| 2008/0290886 A1* | 11/2008 | Akiyama et al. | 324/758 |
| 2009/0211604 A1* | 8/2009 | Winter et al. | 134/18 |

FOREIGN PATENT DOCUMENTS

WO    WO02/089183    11/2002

* cited by examiner

*Primary Examiner* — Jay Patel
*Assistant Examiner* — Francis G Geroleo
(74) *Attorney, Agent, or Firm* — Thorpe North & Western LLP

(57) ABSTRACT

An inspection system for flat objects, especially wafers and dies, including: a handling system for loading objects into the inspection system; a sensor assembly for receiving images or measuring values of the object surface or parts of the object surface; a driving assembly for generating a relative movement between the objects and the sensor assembly, where a movement is effected between objects relative to the sensor assembly along a first trajectory; wherein at least one further sensor assembly is provided, and the driving assembly is adapted to generate a further relative movement, where a movement of different objects relative to the sensor assembly can be generated on at least a second trajectory in order to allow at least two objects to be treated simultaneously.

19 Claims, 7 Drawing Sheets

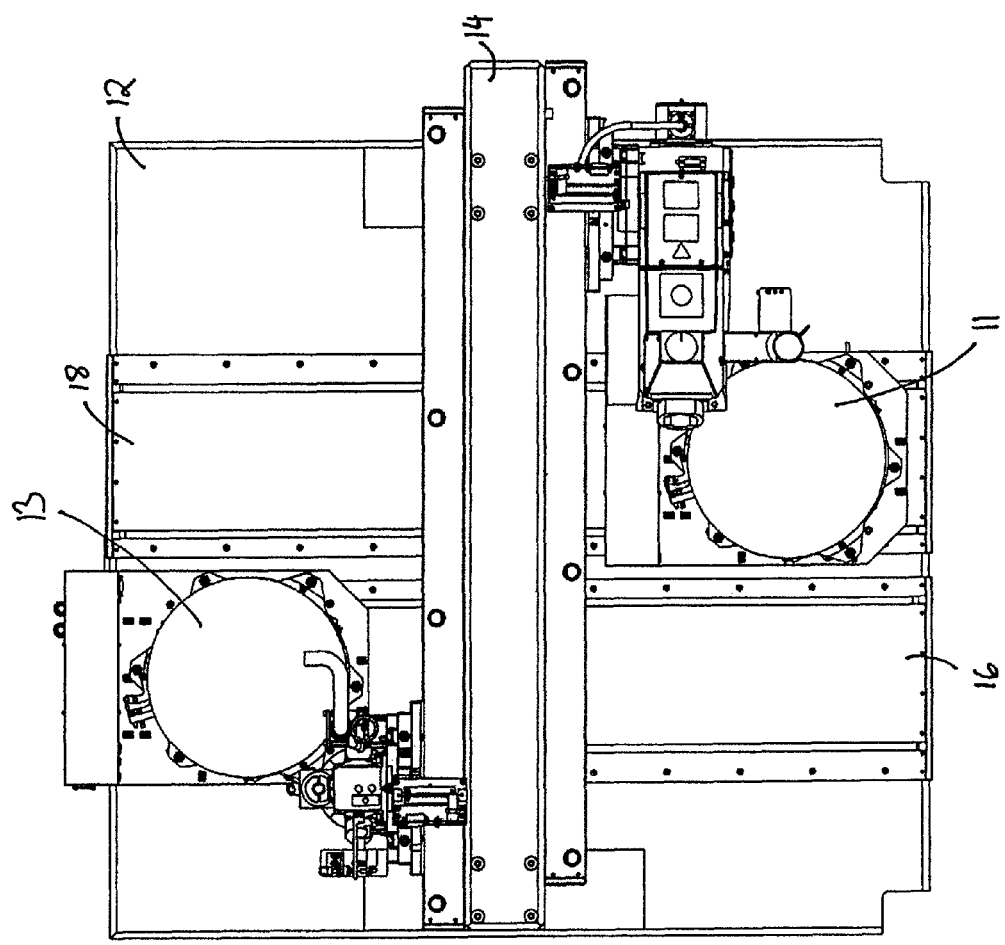

INSPECTION SYSTEM

TECHNICAL FIELD

The invention relates to an inspection system for flat objects, especially wafers and dies, comprising:
(a) a handling system for loading objects into the inspection system;
(b) a sensor assembly for receiving images or measuring values of the object surface or parts of the object surface;
(c) a driving assembly for generating a relative movement between the objects and the sensor assembly, where a movement is effected between objects relative to the sensor assembly along a first trajectory; and
(d) at least one further sensor assembly is provided.

A trajectory is here a time sequence of coordinates representing the movement of an object during a run time. An object may be moved relative to a stationary sensor. However, it is also possible to move a sensor assembly relative to a stationary object. Finally, it is also possible to move the sensor as well as the object relative to each other.

In different industries flat products are inspected regarding defects with optical imaging methods. This may be, amongst others, wafers in the semiconductor- and solar cell industry. Wafers are discs of semiconductor-, glass-, film- or ceramic materials. In certain applications the wafers are typically inspected entirely or at least over large portions of the surface. Such an inspection is called macro-inspection. The lateral resolution required for the recognition of the sought-after defects increases with the further development of the general production technology. Typically resolutions of 5 µm are required in the macro-inspection for the latest technologies. At the same time, devices with a high throughput for inspected wafers are desirable.

Presently, available macro-inspection systems either fulfill the requirements of a high throughput or the desired resolution but not, however, both simultaneously. There is, therefore, the requirement of faster macro-inspection systems with simultaneously improved resolution.

Analogue requirements exist in different industries. Displays must be inspected regarding defects during production in the flat panel industry. Imaging methods often imaging the entire display are used therein for the detection of defects. In the electrical industry circuit boards are inspected regarding defects with optical methods for series of test objects, especially circuit boards.

The need of a quick inspection of a high number of normally similar test objects is a common feature of all these applications. Such objects are circuit boards, wafers, solar cells, displays and the like. The use of sensors for the generation of a large image of the test objects is also a common feature of the applications. Depending on the kind of the sought-after defect, the images may be generated by optical picture-taking systems as well as with point wise operating sensors. Optical picture taking systems are, for example, array- or linear cameras. Point wise operating sensors are, for example, detectors for measuring the reflection of optical rays, microwaves or sound waves. Magnetic sensors may also be used.

PRIOR ART

US 2006/0119366A1 (Iffland) discloses an inspection system with a loading unit and a device for the simultaneous inspection of the front—and the backside of an object.

WO 02/089183A2 (Leica Microsystems Jena GmbH) discloses a holder for objects having two grips mounted on an arm which is rotatable by 180°.

US 2008/0231301 A1 discloses an electric inspection apparatus for aligning a prober with a plurality of electric contacts above a wafer and testing the functionality. As the electric contacts must be exactly positioned an alignment system having two cameras is provided. The alignment system comprises a first camera which is moved along a bridge. In the periphery of the mounting tables an image pickup device is positioned which can be moved together with the table in a rectangular area. The cameras are not the sensors for the inspection itself but only parts of the alignment system. The inspection is carried out with the prober.

DISCLOSURE OF THE INVENTION

It is an object of the invention to provide an inspection system which allows objects to be inspected quicker and with higher resolution. According to the invention this object is achieved with an assembly mentioned above, wherein
(e) the driving assembly is adapted to generate a further relative movement, where a movement of different objects relative to the sensor assembly can be generated on at least a second trajectory in order to allow at least two objects to be treated simultaneously.

With such an assembly several objects may be treated simultaneously without the need of additional, expensive sensor assemblies. The treatment steps comprise especially the loading and adjusting of the objects, the generating of images and the evaluation of such images.

Preferably the objects are moved on two straight, parallel trajectories. The sensor assemblies may also be moved on two straight, parallel trajectories, too. The trajectories of the sensors may extend in such way that the projection is orthogonal to the trajectories of the objects. Such an assembly is, for example, realized by an assembly where the trajectories are formed by stationary tracks each provided with a movable lifting-rotating table guided therein for receiving and adjusting the objects.

The sensor assemblies each can be movably guided in portals arranged above the trajectories of the objects. In other words: the objects are parallely moved in an X-direction and the sensor assemblies are parallely moved above in a Y-direction.

While one of the objects is imaged by the sensors a further object may be simultaneously loaded or imaged by another sensor. Thereby the sensors are particularly well occupied and the throughput of objects is increased.

Preferably the sensor assemblies comprise at least one microscope head. The microscope head preferably has several magnification stages. Furthermore, the sensor assemblies can comprise at least one scanning head. In a particularly preferred modification of the invention one microscope head and one scanning head is provided.

A microscope head (also denoted below with the term micro head) is understood to be an inspection head with a microscope. The microscope especially comprises a camera system for taking microscopic detailed images as well as for carrying out preparatory operations. Such preparatory operations are in particular the adjustment of the wafer, the determination of the focal plane, the determination of the bending of the wafer when inspected on the back side and the bending of wafers which are supported only on their edges. Such a camera system preferably comprises a color camera.

A scanning head is understood to be an inspection head with a macro objective. Furthermore, a camera system is provided which may be used to scan the entire wafer or large portions thereof. Such a camera system may be realized by an array camera or a line scan camera. Such a camera system preferably comprises a color camera.

A full automatic inspection of the entire wafer is realized especially with wafer inspections with a combination of a microscope head and a scanning head. The inspection may be used for the independent evaluation of the wafer as well as a basis for a subsequent review by means of the second sensor assembly in the form of a microscope. When a suitable combination of sensors is used a resolution in the lower µm-range can be achieved. No detection gap occurs with the combination with an automatic microscope inspection.

In an alternative modification of the invention two or more scanning heads are used. In a further modification of the invention two or more microscope heads are used. Such modifications can cause an increased throughput depending on their application. Also, a black and white-camera can be used as a sensor assembly instead of a color camera.

In a further modification of the invention a microscope head is used on the first sensor head trajectory and two scanning heads are used on the second sensor head trajectory sharing one guiding unit. Such guiding units consisting of a guiding, passive driving components and two independently controlled actively driven, mobile carriers are commercially available from, for example, Aerotech, Inc.

In this modification the microscope head is exclusively used for preparatory steps, such as adjustment and determination of the height, while the two scanning heads are used for scanning the objects. With such an assembly a particularly high throughput can be achieved by abandoning the option of taking detailed microscopic images.

Preferably at least one of the sensor assemblies is an array sensor with a two-dimensional array of detector elements.

A method according to the invention for carrying out an inspection of a plurality of flat objects, especially wafers and dies, with such an inspection system comprises the steps of:
(a) loading an object into the inspection system for movement on a first trajectory;
(b) taking at least one image or measuring value of the object or a portion of the object with a first sensor assembly; and
(c) taking a further image or a further measuring value of the object or a portion of the object with a second sensor assembly;

The method is characterized in that
(d) during the carrying-out of steps (a) to (c) another step of (a) to (c) is carried out on another object moving on a second trajectory, and
(e) steps (b) and (c) are carried out with the same sensor assemblies as with the object on the first trajectory.

The method has proven to be particularly advantageous if one sensor is a micro-head and one sensor is a scanning head and corresponding steps on the trajectories are carried out with a delay. A method can be as follows:
(a') loading a first object into the inspection system for movement on a first trajectory;
(b') adjusting the first object using the first sensor assembly in the form of a micro head and partially simultaneous loading of a second object into the inspection system for movement on a second trajectory;
(c') moving the first object to the second sensor assembly in the form of a scanning head;
(d') taking an image of the first object or at least a portion of the object with the scanning head and at least partially simultaneous adjusting the second object using the micro-head;
(e') returning the first object to the micro head and at least partially simultaneous moving the second object to the scanning head;
(f') taking an image of the second object with the scanning head;
(g') unloading the first object;
(h') returning the second object to the micro-head and discharging the object and at least partially simultaneous repeating steps (a') to (g') while further objects are provided for inspection.

Optionally one or more further detailed images of the first object can be taken simultaneous to step (f'). Furthermore, optionally a detailed image of the second object can be taken while an object is loaded for movement on the first trajectory. A full image taken with a scanning head or a partial image of a wafer can be assembled from several individual images. Selected points are aimed at by the micro head and the individual images are taken.

The present invention is particularly suitable for the inspection of wafers in the semiconductor industry. However, it is not limited thereto. An inspection may also be carried out with the invention with portions, fractions and other flat objects, such as, for example, solar cells, printed circuit boards, displays, printed structures.

Furthermore, the invention is not limited to a certain detection method. It may be implemented with either bright field or dark field detection. Preferably a mixed illumination combines the advantages of both imaging methods. Furthermore different known imaging methods may be used, such as, for example, interference contrast imaging (DIC), Imaging using the polarization of light or con-focal images. Also a front- and/or back side inspection can be carried out for each object on both trajectories.

It does not have any impact on the usefulness of the invention if individual images are taken or measurements are made with the sensor assemblies during a continuous movement on the trajectories or if the movement is stopped for each image or measurement. In particular, a camera assembly in the form of a scanning head can stop either for each image taking at a pair of coordinates or the image can be taken during continuous movement using a flash light or a suitably quick shutter.

It is understood that images and measuring values can be taken with the sensor assemblies either for the entire surface or for portions thereof without deviating from the idea of the invention. Also the amount of images or measuring values is optional.

Further modifications of the invention are subject matter of the subclaims. An embodiment is described below in greater detail with reference to the accompanying drawings.

BRIEF DESCRIPTION OF THE DRAWINGS

FIG. 7 corresponds to the representation of FIG. 1 with wafer.

DESCRIPTION OF AN EMBODIMENT

Figure 1:
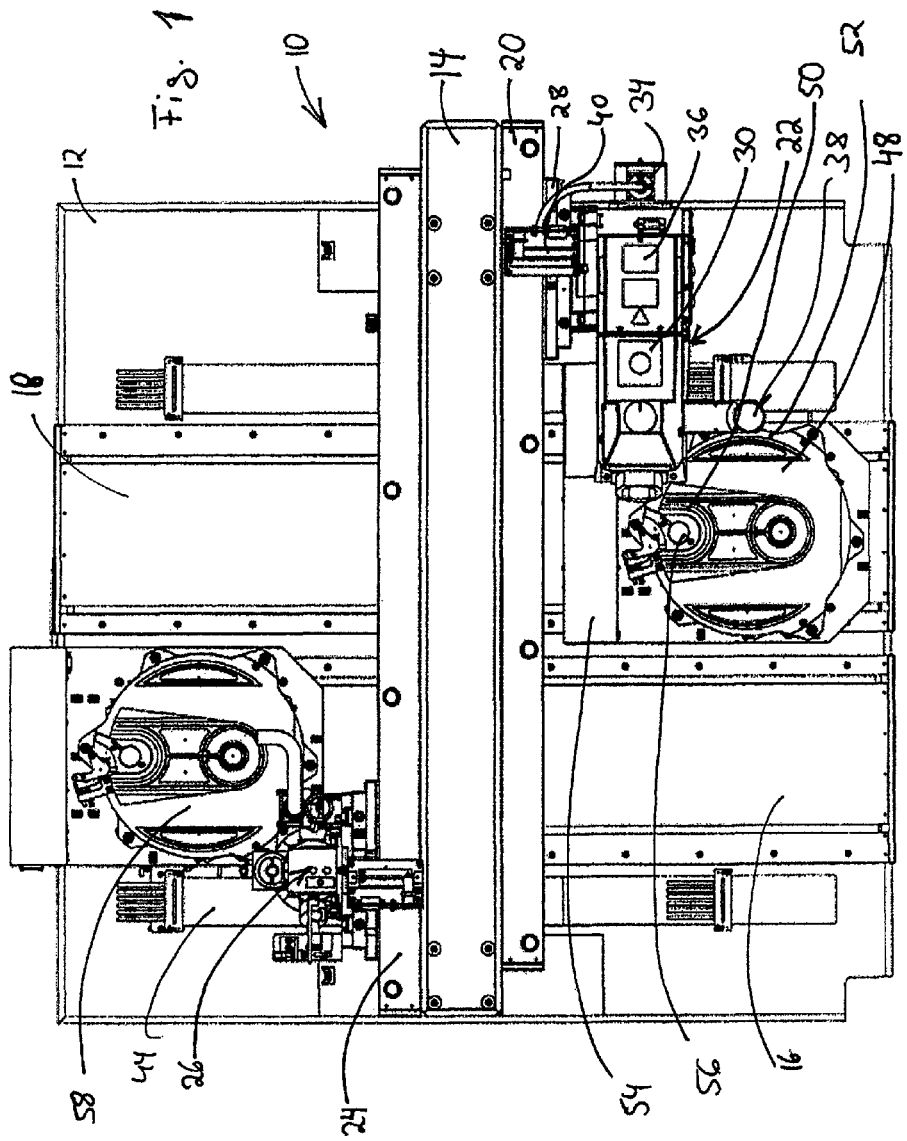
FIG. 1 is a top view of an inspection system for wafers.
Figure 2:
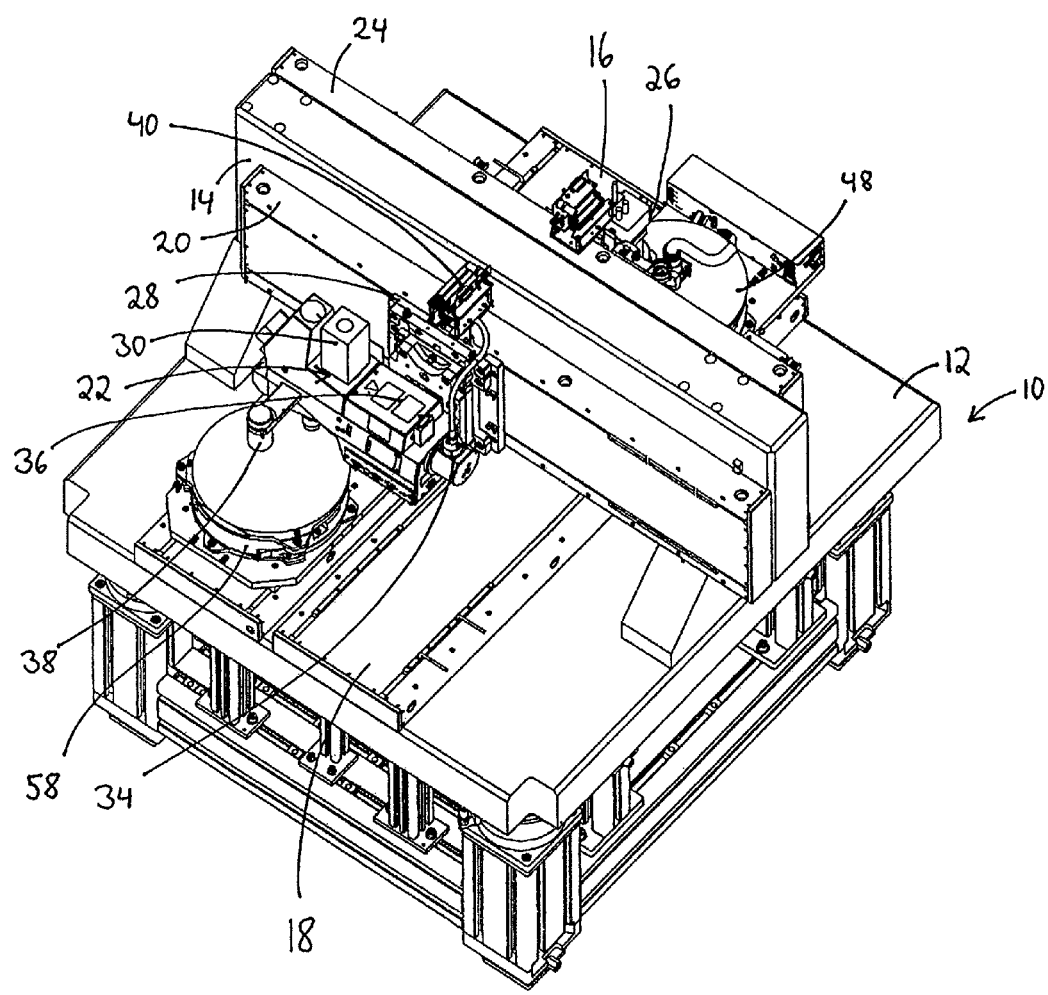
FIG. 2 shows the inspection system of FIG. 1 as a perspective view.

In the figures an inspection system for wafers 11, 13 is shown which is generally denoted with numeral 10. The inspection system 10 comprises a two-dimensional, plane granite base 12. A granite portal 14 is fixed to the granite base 12. The granite portal 14 extends along the entire length of the granite base 12. The granite portal 14 defines a Y-axis. Two guiding rail systems 16 and 18 are fixed to the granite base 12 below the granite portal 14. The guiding rail systems 16 and 18 run parallel in the direction of an X-axis. The projection of the Y-axis defined by the granite portal 14 is perpendicular to the X-axis.

Peripheral devices which are common for such systems, such as a handling system for loading and unloading, rack 15 (FIG. 6) and housing, filter-airing unit and airing devices as well as the required electronic controller 17 and supply systems which are partly integrated below or above the granite portal system 12, 14 in order to save space are not shown or only partly shown.

A guiding rail 20 extending in Y-direction is fixed to the front side of the granite portal 14, shown on the bottom of FIGS. 1 and 7. A microscope head generally denoted with numeral 22 is movably guided at the guiding rail 20.

A guiding rail 24 extending in Y-direction is fixed to the back side of the granite portal 14, shown on the top of FIGS. 1 and 7. A scanning head generally denoted with numeral 26 is movably guided at the guiding rail 24.

Both guiding systems 20 and 24 are designed in such a way that the requirements of cleanliness of the respective users are fulfilled. This includes the use of guiding and driving devices which generate few particles only, the use of suitable lubricants with small loss of particles, suitable covers of the moving parts, suitable arrangements of unavoidable openings and the possibility of exhausting the inner spaces of the guiding system combined with openings which are kept as small as possible in order to remove the generated particles and thereby prevent their exiting in the direction of the sample (wafer). The same considerations apply to the necessary energy- and signal connections to the movable components as they are mentioned below. The precision of positioning required for this method is ensured by the use of suitably designed guiding bodies as well as by the used positioning measuring systems.

Figure 5:
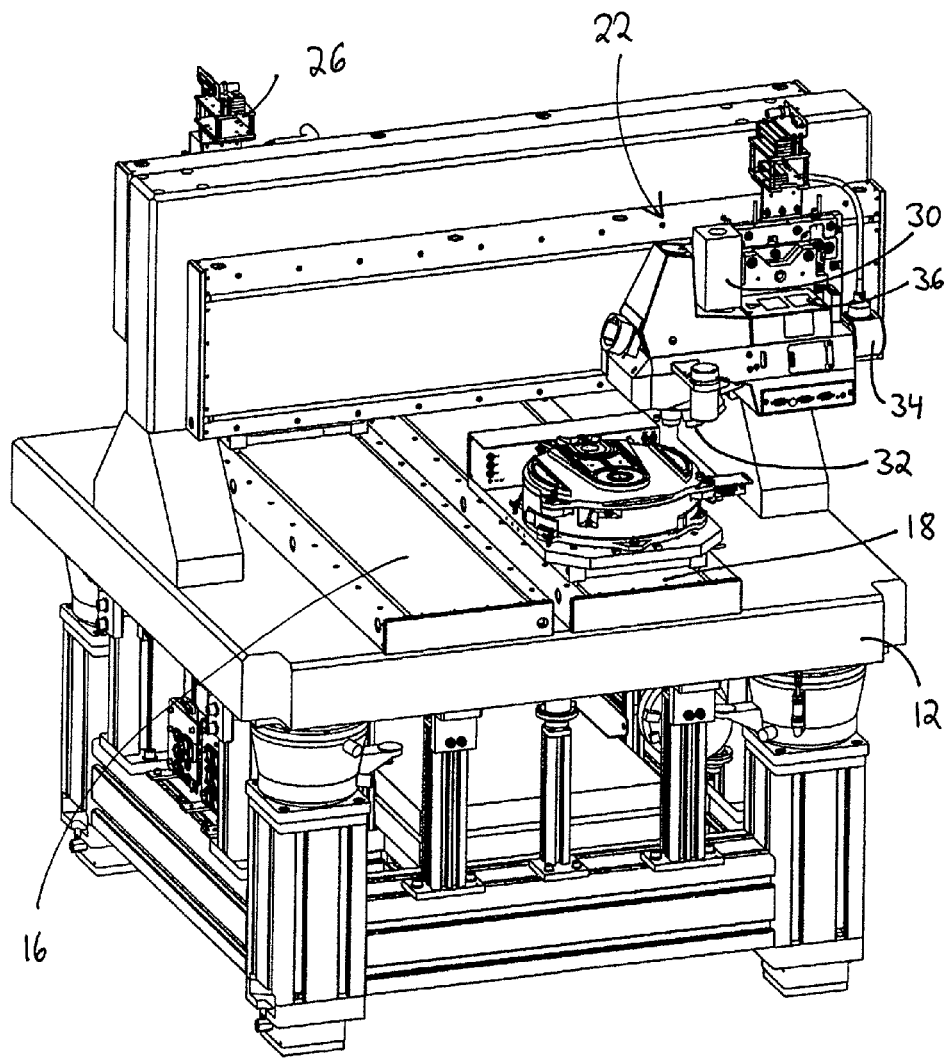
FIG. 5 shows the inspection system of FIG. 4 in a different perspective from the front.

The microscope head 22 comprises a slide 28 guided on the guiding rail 20. The slide comprises adjusting means for adjusting the microscope regarding the observed range. In order to facilitate servicing the adjusting means are designed in such a way that the head can be removed by releasing a few fixing elements without destroying the adjustment so that normally no new adjustment is necessary upon remounting of the head. The microscope comprises all common component necessary for a reflected-light microscope, especially an illuminating optical path with a field- and aperture stop, filters, devices for homogenizing the illumination and introducing of light into the objective as well as an imaging optical path with the required imaging optics to image the object (wafer surface) to the sensor plane of the camera. Thereby, it is possible to fully fulfill the imaging conditions according to Köhler. A camera 30 is mounted on the microscope. An array detector may be used in this embodiment as well as a line-detector. An image of the observed range is imaged to the imaging plane of the camera 30 by means of microscope objectives 32 (shown in FIG. 5). The illumination of the observed area is effected by means of light which is coupled into the camera beam path by an optical fiber. For this purpose an interface 34 is provided which adapts the light from the optical fiber to the beam conditions in the microscope by means of a collimator. Furthermore a laser-autofocus 36 and an analyzer-unit 38 for DIC contrast are provided in the microscope head 22. The laser-autofocus 36 reflects a laser beam into the optical arrangement of the microscope and evaluates the reflected beam. Thereby, it is possible to check online if the observed surface of the object is in the focal plane of the microscope. In such a way an adjustment of the table can be effected by back-coupling with the lifting system of the table (shown below) and the condition for a well focused image is fulfilled. The analyzer-unit 38 together with a polarizer element in the microscope serve to possibly use the differential interference contrast method for imaging. In principle the microscope can be upgraded with further components to use further imaging—and measuring methods. Energy supply and signal transmission are effected through a flexible ribbon cable, which is connected to a termination fitting 40. The ribbon cable fulfills the necessary requirements regarding cleanliness and is frictionless guided. The used optical fibers are separately guided without contact to other components in order to maintain a small particle emission while freedom of friction and large bending diameters are realized.

Figure 6:
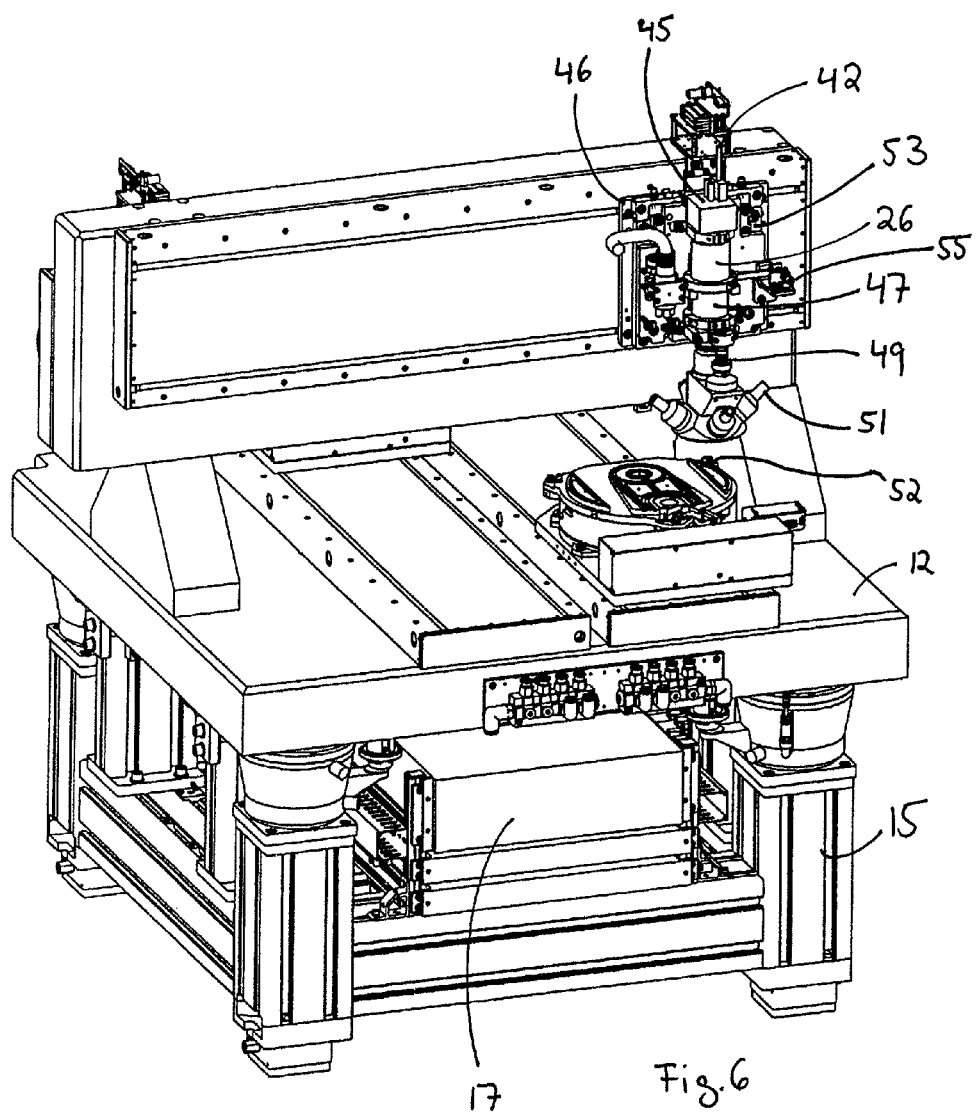
FIG. 6 shows the inspection system of FIG. 5 in a different perspective from the rear.

In the representation of FIG. 6 the scanning head 26 can be recognized. The scanning head 26 is also connected to the electronic equipment—not shown—through a flexible ribbon cable 44. A termination fitting 42 is provided for this purpose. The scanning head 26 is fixed to a guiding slide 46 which is adapted to be moved in a Y-direction at the granite portal 14. The scanning head comprises the main components camera 45, objective 47, light coupling for bright field illumination 49, light coupling for dark field illumination 51 and adjusting and fixing elements 53. The light couplings use optical fibers to keep the moved overall-mass small. The dark field light is divided upon several optical fiber arms and the observed area is illuminated by correspondingly many light spots. The illumination with light is effected with an angle from several sides to ensure homogeneity of the illumination.

A very fine adjustment means 55 for rotating the camera in the moving direction of the scanning head during scanning is provided as an adjustment element in addition to the device for vertical adjustment of the optical axis with respect to the wafer surface, in order to ensure in cooperation with the angle adjustment of the wafer that the camera image (or line detector) and the main structure axes of the wafer are parallel, because artifacts in the image processing can be caused by relative rotation.

A wafer table 48 is movably guided in the guiding rail system 18. The wafers which shall be inspected are installed on the wafer table 48 with a commercially available handling system (not shown). The wafer table 48 has a support with vacuum suction channels for supporting the wafers and fixing it during front side inspection. Furthermore, the wafer table 48 is provided with a clamping device 50 and several supporting points 52 only touching the wafer edge for the backside inspection. These supporting points are offset to the support for the front side inspection so that the supporting devices or the supported wafers do not disturb each other. The wafer is held thereon by the clamping device 50. The wafer table 48 is provided with motorized lifting- and rotating means for adjusting the wafer. The position of the wafer can be adjusted with the rotating means in such a way that the scanning head is guided exactly parallel to the main structure axes on the wafer during scanning of the wafer. Different wafers can be brought into the focal plane of the optical arrangement of the microscope or scanning head, respectively, by means of the lifting device. Furthermore, especially bent wafers, can be adjusted in height, for example, during back side inspection, so that the position of the wafer in the focal height when an image is taken is ensured during the entire treatment. A table controller 54 controls and coordinates the movement of the table in the direction of the guiding rail system 18 (X-direction). Furthermore, a wafer presence sensor 56 is provided, which ensures together with the vacuum recognition and the feedback of the position of the clamping device 50 a high safety for the recognition of the presence and the correct fixing of the position of the wafer.

A wafer table 58 is movably guided in the guiding rail system 16. The wafer table 58 is identical to the wafer table 48 and, therefore, need not be described here in greater detail.

Figure 3:
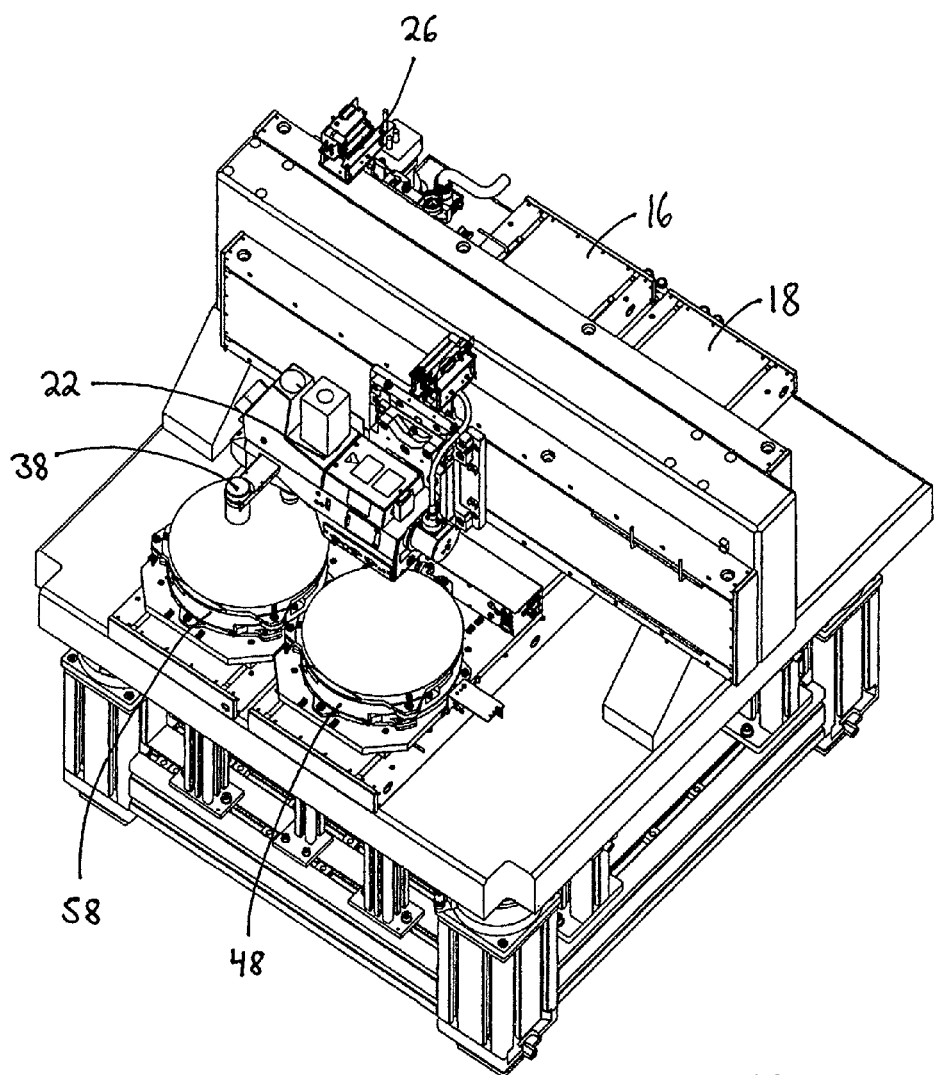
FIG. 3 shows the inspection system of FIGS. 1 and 2 in a different inspection phase.
Figure 4:
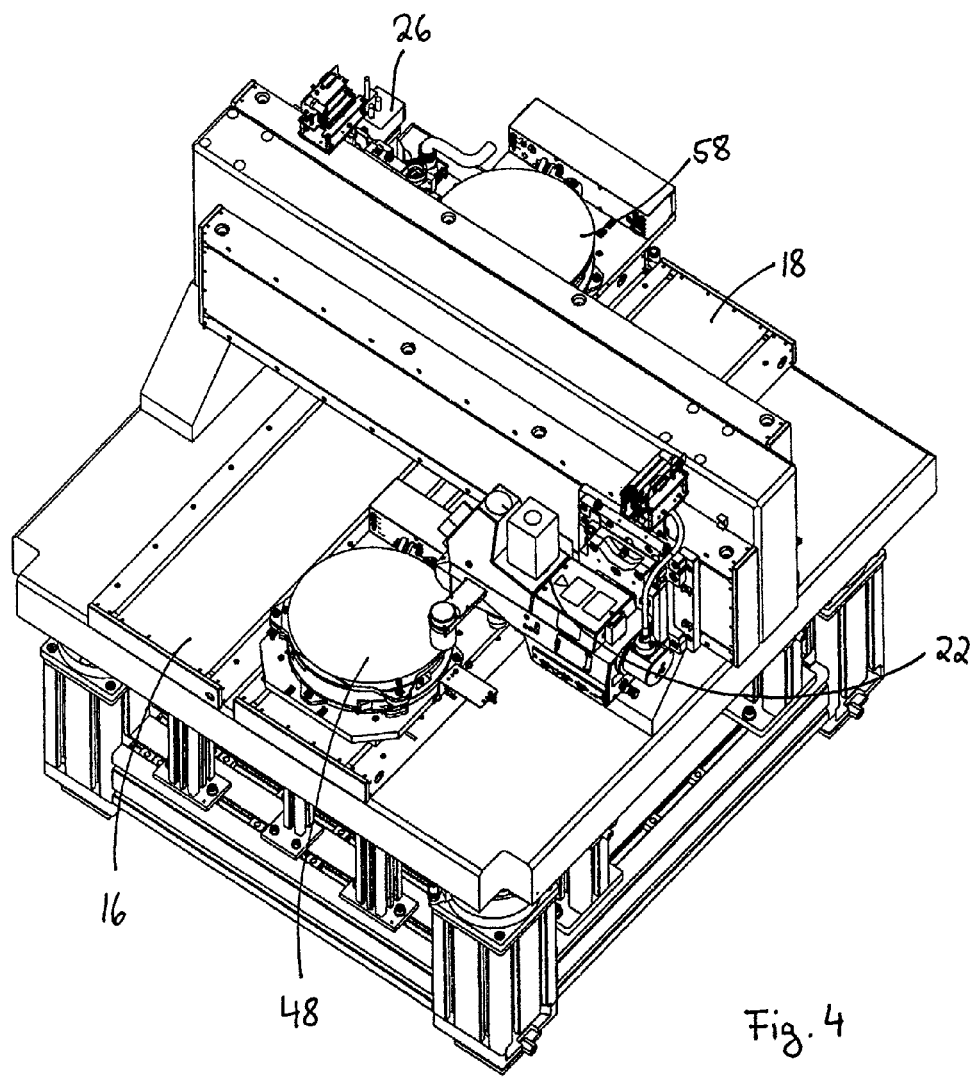
FIG. 4 shows the inspection system of FIGS. 1 to 3 in a further inspection phase.

The described assembly operates as follows:

Initially, the wafer tables 48 and 58 are in an end position as it is shown in FIG. 3. The handling system (not shown) puts a wafer, which shall be inspected, on the wafer table 58. The wafer is then adjusted by means of the microscope head 22 (registration of the wafer) and adjusted in height. For this purpose the microscope head 22 is moved in Y-direction until it is positioned above the guiding rail system 16. After the adjustment the wafer table 58 is moved together with the wafer in the guiding rail system 16 to the position shown in FIG. 4. The scanning head 26 is moved in Y-direction until it is positioned above the guiding rail system 16. In this position the wafer on the wafer table 58 is scanned with the scanning head 26. One or more images of the entire wafer or large portions of the wafer are taken. At the same time or shortly before or after the microscope head 22 is moved in Y-direction until it is positioned above the guiding rail system 18 to operate on the wafer already put in place by the handling system. This is shown in FIG. 4. The wafer on the wafer table 48 is also adjusted by means of the microscope head 22 laterally and in height. After the scanning is finished the first wafer on the wafer table 58 is unloaded. For this purpose the wafer table 58 is moved in X-direction back to the initial position. Alternatively, more detailed images can be taken by means of the microscope head 22 before the wafer on the wafer table 58 is unloaded. At the same time or shortly before or after the wafer table 48 is moved in X-direction until it is positioned below the scanning head 26. Simultaneously the scanning head 26 is moved in Y-direction until it is positioned above the guiding rail system 18. This position corresponds to the situation in FIG. 4, only that the position of the wafer tables 48 and 58 are exchanged and the position of the scanning head 26 is exchanged with the position of the microscope head 22. In this position the wafer on the wafer table 48 is scanned and a third wafer is put on the wafer table 58. The steps described above are repeated until all wafers are inspected.

In the present embodiment the first wafer was put on the wafer table 58. It is understood, however, that the procedure can be started as well with the identical wafer table 48.

In different embodiments a microscope head is used instead of the scanning head 26. This is useful if only small ranges of the wafer must be inspected.

The described sequence of operating steps is modified in various embodiments, if, for example, when two micro heads or two scanning heads are used on a common axis without deviating from the principle idea of the invention.

The invention claimed is:

1. An inspection system for flat objects, said objects having an object surface, comprising:
   (a) a first holder for holding one of said objects for inspection system;
   (b) a second holder for holding another of said objects for inspection;
   (c) a first sensor assembly for receiving images or measuring values of said object surface or a portion of said object surface;
   (d) a second sensor assembly for receiving images or measuring values of said object surface or a portion of said object surface;
   (e) a driving assembly for generating a relative movement between said first holder and said first and second sensor assemblies wherein a movement is effected between said first holder relative to said first and second sensor assemblies along a first trajectory and for generating a relative movement between said second holder and said first and second sensor assemblies wherein a movement is effected between said second holder relative to said first and second sensor assemblies along a second trajectory; and
   wherein
   (f) said movement effected by said driving assembly between said first holder relative to said first and second sensor assemblies is adapted to generate relative movement of said first holder along said first trajectory between a first trajectory first position wherein images or measuring values of said object surface or a portion of said object surface of said flat object held by said first holder are received by said first sensor assembly and said first holder adjusts the object held thereby using said first sensor assembly and to a first trajectory second position wherein said first holder and said second sensor assembly are in positions wherein images of said object surface or a portion of said object surface of said flat object held by said first holder are received by said second sensor assembly, and said movement effected by said driving assembly between said second holder relative to said first and second sensor assemblies is adapted to generate relative movement of said second holder along said second trajectory between a second trajectory first position wherein images or measuring values of said object surface or a portion of said object surface of said flat object held by said second holder are received by said first sensor assembly and said second holder adjusts the object held thereby using said first sensor assembly and to a second trajectory second position wherein said second holder and said second sensor assembly are in positions wherein images of said object surface or a portion of said object surface of said flat object held by said second holder are received by said second sensor assembly, and such movement is coordinated so that when said first holder is in said first trajectory first position said second holder is in said second trajectory second position, and vice versa, in order to allow at least two objects to be treated simultaneously with said sensor assemblies.

2. The inspection system according to claim 1, wherein said first and second trajectories are two straight, parallel trajectories.

3. The inspection system according to claim 2, wherein said sensor assemblies are moved on two straight, parallel trajectories and extend in such way that said projection is orthogonal to the first and second trajectories.

4. The inspection system according to claim 1, wherein said sensor assemblies are moved on two straight, parallel trajectories.

5. The inspection system according to claim 1, wherein said sensor assemblies comprise at least one microscope head.

6. The inspection system according to claim 1, wherein said sensor assemblies comprise at least one scanning head.

7. The inspection system according to claim 1, wherein said first and second holders are each a lifting and rotating table which is moveably guided for receiving and adjusting the objects.

8. The inspection system according to claim 1, wherein said sensor assemblies are each moveably guided on a portal beam located above the first and second trajectories of said holders.

9. The inspection system according to claim 1, wherein at least one of said sensor assemblies is a black-and-white camera or a color camera.

10. The inspection system according to claim 1, wherein at least one of said sensor assemblies is an array sensor with a two-dimensional array of detector elements.

11. The inspection system according to claim 1, wherein said sensor assemblies are carried on an axis and one of said axes carrying a sensor assembly is equipped with two independently controllable sensor assemblies.

12. The inspection system according to claim 1, wherein said inspection system is adapted to inspect wafers or dies and said first and second holders are adapted to hold wafers or dies.

13. Method for carrying out an inspection of a plurality of flat objects, comprising the steps of
   (a) loading one of said objects into an inspection system for movement on a first trajectory;
   (b) taking at least one image or measuring value of said first one object or a portion of said one object with a first sensor assembly and adjusting said one object using said first sensor assembly, and partially simultaneously loading another object into the inspection system for movement on a second trajectory;
   (c) moving said one object to a second sensor assembly;
   (d) taking a further image or a further measuring value of said one object or a portion of said one object with said second sensor assembly, and at least partially simultaneous taking at least one image or measuring value of said another object or a portion of said another object with said first sensor assembly and adjusting said another object using said first sensor assembly;
   (e) returning said one object to said first sensor assembly and at least partially simultaneous moving said another object to said second sensor assembly;
   (f) taking a further image or a further measuring value of said another object or a portion of said another object with said second sensor assembly;
   (g) unloading said one object;
   (h) returning said another object to said first sensor assembly and unloading said another object, and at least partially simultaneous repeating steps (a) to (h) while further objects are provided for inspection.

14. Method according to claim 13, wherein a detailed image of said first one object is taken simultaneous to step (f).

15. Method according to claim 14, wherein a detailed image of said another object is taken while a further object is loaded for movement on said first trajectory.

16. Method according to claim 13, wherein a detailed image of said another object is taken while a further object is loaded for movement on said first trajectory.

17. Method according to claim 13, wherein said flat objects are wafers or dies.

18. Method according to claim 13, wherein the steps of taking at least one image or measuring value with a first sensor assembly are the steps of taking at least one image or measuring value with microscope head.

19. Method according to claim 13, wherein the steps of taking at least one image or measuring value with a second sensor assembly are the steps of taking at least one image or measuring value with scanning head.

* * * * *